United States Patent
Roy et al.

(10) Patent No.: US 11,590,062 B2
(45) Date of Patent: Feb. 28, 2023

(54) HAIR COSMETIC COMPOSITION COMPRISING SILICONES AND SURFACTANTS, AND COSMETIC TREATMENT PROCESS

(71) Applicant: L'Oreal, Paris (FR)

(72) Inventors: Dhimoy Roy, Mumbai Maharashtra (IN); Maxime Deboni, Shanghai (CN); Sarish Joshi, Mumbai Maharashtra (IN)

(73) Assignee: L'Oreal, Paris (FR)

( * ) Notice: Subject to any disclaimer, the term of this patent is extended or adjusted under 35 U.S.C. 154(b) by 961 days.

(21) Appl. No.: 16/063,972

(22) PCT Filed: Dec. 20, 2016

(86) PCT No.: PCT/EP2016/081975
§ 371 (c)(1),
(2) Date: Jun. 19, 2018

(87) PCT Pub. No.: WO2017/108824
PCT Pub. Date: Jun. 29, 2017

(65) Prior Publication Data
US 2020/0268621 A1    Aug. 27, 2020

(30) Foreign Application Priority Data
Dec. 21, 2015 (IN) .......................... 4775/mum/2015

(51) Int. Cl.
| | | |
|---|---|---|
| *A61K 8/06* | (2006.01) | |
| *A61K 8/34* | (2006.01) | |
| *A61K 8/41* | (2006.01) | |
| *A61K 8/46* | (2006.01) | |
| *A61K 8/86* | (2006.01) | |
| *A61K 8/891* | (2006.01) | |
| *A61K 8/898* | (2006.01) | |
| *A61Q 5/02* | (2006.01) | |
| *A61Q 5/12* | (2006.01) | |

(52) U.S. Cl.
CPC .............. *A61K 8/062* (2013.01); *A61K 8/345* (2013.01); *A61K 8/416* (2013.01); *A61K 8/463* (2013.01); *A61K 8/466* (2013.01); *A61K 8/86* (2013.01); *A61K 8/891* (2013.01); *A61K 8/898* (2013.01); *A61Q 5/02* (2013.01); *A61Q 5/12* (2013.01); *A61K 2800/21* (2013.01); *A61K 2800/412* (2013.01); *A61K 2800/413* (2013.01); *A61K 2800/5422* (2013.01); *A61K 2800/5424* (2013.01); *A61K 2800/5426* (2013.01); *A61K 2800/5428* (2013.01); *A61K 2800/594* (2013.01); *A61K 2800/596* (2013.01)

(58) Field of Classification Search
CPC ...................................................... A61K 8/062
See application file for complete search history.

(56) References Cited

U.S. PATENT DOCUMENTS

| | | | |
|---|---|---|---|
| 8,546,483 B2 * | 10/2013 | Tanaka ..................... | A61Q 5/02 |
| | | | 524/838 |
| 2013/0177516 A1 * | 7/2013 | Tamura .................. | A61K 8/893 |

FOREIGN PATENT DOCUMENTS

| | | | |
|---|---|---|---|
| EP | 1010717 A2 | 6/2000 | |
| JP | 2008-521936 | 6/2008 | |
| JP | 2009-221450 | 10/2009 | |
| JP | 2013-532741 | 8/2013 | |
| JP | 2015-110538 | 6/2015 | |
| JP | 2019-501981 | 1/2019 | |
| KR | 10-2010-0126511 | 12/2010 | |
| WO | WO99/24004 | * 5/1999 | ............... A61K 7/06 |
| WO | 2009/116689 A1 | 9/2009 | |
| WO | 2015/082358 A1 | 6/2015 | |
| WO | WO 2017/109692 | 6/2017 | |

OTHER PUBLICATIONS

Dow Corning, cheminudstry, Chemical Information Search, Dow Corning 1664, downloaded in Mar. 2022 (Year: 2022).*
(Universal Selector, Dowsil 1664 Emulsion, Technical Datasheet, downloaded in Mar. 2022 (Year: 2022).*

* cited by examiner

*Primary Examiner* — Mark V Stevens
*Assistant Examiner* — Alparslan Asan
(74) *Attorney, Agent, or Firm* — Bret E. Field; Bozicevic, Field & Francis LLP

(57) ABSTRACT

The present invention relates to a hair cosmetic composition, especially for washing and/or conditioning hair, comprising surfactants and an oil-in-water emulsion that comprises:
  a silicone mixture comprising a trialkylsilyl terminated dialkylpolysiloxane and an amino silicone;
  a mixture of emulsifiers comprising one or more nonionic emulsifier, wherein the mixture of emulsifiers has a HLB value from 10 to 16; and
  water.

The invention also relates to a process for the cosmetic treatment of hair, preferably for washing and/or conditioning hair, using this composition.

16 Claims, No Drawings

HAIR COSMETIC COMPOSITION COMPRISING SILICONES AND SURFACTANTS, AND COSMETIC TREATMENT PROCESS

The present invention relates to hair cosmetic compositions, such as compositions for caring hair, more particularly for washing and/or conditioning hair, and preferably shampoos. The invention also relates to a cosmetic process for washing and/or conditioning hair, using this composition.

It is common practice to use detergent and conditioning hair care compositions, such as shampoos, based essentially on surfactants, for washing keratin materials such as the hair. These compositions are applied to the keratin materials, which are preferably wet, and the lather generated by massaging or rubbing with the hands makes it possible, after rinsing with water, to remove the diverse types of soiling initially present on the hair.

These compositions contain substantial contents of "detergent" surfactants, which, in order to be able to formulate cosmetic compositions with good washing power, must especially give them good foaming power. The surfactants that are useful for this purpose are generally of anionic, nonionic or amphoteric type, and particularly of anionic type. Admittedly these compositions are of good washing power, but the intrinsic cosmetic properties associated with them nevertheless remain fairly poor, owing in particular to the fact that the relatively aggressive nature of such a cleaning treatment can, in the long run, lead to more or less pronounced damage to the hair fiber, this damage being associated in particular with the gradual removal of the lipids or proteins contained in or on the surface of this fiber.

Thus, in order to improve the cosmetic properties of the above detergent compositions, and more particularly those which are to be applied to sensitized hair (i.e. hair which has been damaged, weakened or made brittle, in particular through the chemical action of environmental agents and/or hair treatments such as permanent-waving, dyeing or bleaching), it is known to introduce into these compositions additional cosmetic agents known as conditioners (or conditioning agents).

The main purpose of these conditioning agents is to repair, rectify or limit the undesirable effects induced by the various treatments or aggressions to which the hair fibers are subjected to, more or less repeatedly. These conditioning agents may, of course, also improve the cosmetic behavior of natural hair.

The most commonly used conditioning agents are cationic polymers, silicones and silicone derivatives, which impart to washed, dry or wet hair an ease-of disentangling, a softness and a smoothness which are markedly better than that which can be obtained with corresponding cleansing compositions which do not contain them It is known, for example from U.S. Pat. No. 6,417,145, to use a mixture of silicone and cationic polymer in a shampoo, to wash and condition the hair. However, these compositions still have numerous disadvantages, such as presenting a low foam power and leading to an insufficient deposit of silicones on hair impacting therefore strongly on their cosmetic properties.

It is also known, for example from U.S. Pat. No. 6,610,280, a hair treatment composition containing a silicone component comprising droplets of silicone blend, said silicone blend comprising from 50 to 95% by weight of a first silicone having a viscosity of at least 100,000 mm²/sec and from 5 to 50% by weight a second silicone which is functionalized, for example amino-functionalized silicones.

But these compositions are not completely satisfactory. The silicone emulsions currently used in personal care compositions usually comprise high viscosity silicones that give a good smoothness and feel properties but have the disadvantage of giving heavy feel and build-up on the hair, and incur problem during removal from the hair while rinsing.

Also, the emulsions that are used in the prior art are mainly big blob emulsions and hence the silicone deposition is not very uniform, and the desired performance is not achieved.

Thus, there is a real need to provide cosmetic compositions, such as compositions for washing and/or conditioning hair, that do not have the combination of drawbacks described above, i.e. which can give high levels of foam and enhance cosmetic properties of said fibers, namely by affording them softness, smoothness and disentangling.

The composition should trigger satisfactory silicone deposit on the keratin fibers and should also have good detergent properties.

There is a need for a lower viscosity silicone(s) emulsion that will have similar good feel and smoothness properties as higher viscosity silicone emulsions, together with a reduced heavy feel and build-up.

It is basically an objective of this invention to provide a hair composition comprising an emulsion containing a preferably low viscosity silicone, or mixture thereof, with a low emulsion particle size, said emulsion being mechanically stable.

The Applicant has now discovered that the use of a specific emulsion comprising silicones, especially in a shampoo base, makes it possible to achieve the objectives outlined above.

Thus, one object of the invention is especially a hair composition comprising:
(i) one or more surfactants preferably chosen from anionic surfactants, nonionic surfactants, amphoteric surfactants, and mixture thereof, and
(ii) an oil-in-water emulsion having $D_{50}$ particle size of less than 350 nm and comprising:
  a silicone mixture comprising (i) a trialkylsilyl terminated dialkylpolysiloxane having a viscosity of from 40,000 to less than 100,000 mPa·s at 25° C. and (ii) an amino-silicone having a viscosity of from 1,000 to 15,000 mPa·s at 25° C. and an amine value of from 2 to 10 mg of KOH per gram of amino-silicone;
  a mixture of emulsifiers comprising one or more nonionic emulsifiers, wherein the mixture of emulsifiers has a HLB value from 10 to 16; and
  water,
wherein the oil-in-water emulsion is present in the hair composition in a quantity ranging of from 0.1% to 15% by weight with respect to the total weight of the hair composition.

Another object of the present invention is a process for the cosmetic treatment of hair, preferably for washing and/or conditioning hair, comprising the steps of applying to the hair, preferably in a wet state, the hair composition described above, and optionally rinsing them with water after an optional period of exposure.

The composition according to the invention makes it possible to generate abundant foam of very good quality. It especially provides homogeneous foam which has good persistence over time. Furthermore, the foam formed from the composition according to the invention spreads easily and uniformly on hair.

Furthermore, the composition according to the present invention is able to deposit a high amount of silicones on the hair, even when the composition contains a small amount of silicones, and this with no impact on the foam, especially on its quality or its quantity.

In addition, the composition according to the invention leads to improved cosmetic properties, and especially affords good conditioning of the hair, including when the hair is sensitized. Indeed, the composition of the invention provides, for instance, smoothness, softness and disentangling to the hair.

In that which follows and unless otherwise indicated, the limits of a range of values are included within this range, in particular in the expressions "of between" and "ranging from . . . to . . . ".

Moreover, the expressions "at least one" or "at least a" used in the present description are equivalent to the expression "one or more".

A—Surfactants

The cosmetic composition according to the invention is preferably a hair shampoo composition.

The cosmetic composition according to the invention comprises at least one surfactant, which is preferably selected from the group consisting of anionic, nonionic and amphoteric surfactants, or a mixture thereof.

i) Anionic Surfactants

The term "anionic surfactant" means a surfactant comprising, as ionic or ionizable groups, only anionic groups.

In the present description, a species is termed as being "anionic" when it bears at least one permanent negative charge or when it can be ionized as a negatively charged species, under the conditions of use of the composition of the invention (for example the medium or the pH) and not comprising any cationic charge.

The anionic surfactants may be sulfate, sulfonate and/or carboxylic (or carboxylate) surfactants. Needless to say, a mixture of these surfactants may be used.

The carboxylic anionic surfactants that may be used thus comprise at least one carboxylic or carboxylate function (—COOH or —COO—).

They may be chosen from the following compounds: acylglycinates, acyllactylates, acylsarcosinates, acylglutamates; alkyl-D-galactosideuronic acids, alkyl ether carboxylic acids, alkyl(C6-30 aryl) ether carboxylic acids, alkylamido ether carboxylic acids; and also the salts of these compounds;

the alkyl and/or acyl groups of these compounds comprising from 6 to 30 carbon atoms, especially from 12 to 28, better still from 14 to 24 or even from 16 to 22 carbon atoms; the aryl group preferably denoting a phenyl or benzyl group;

these compounds possibly being polyoxyalkylenated, especially polyoxyethylenated, and then preferably comprising from 1 to 50 ethylene oxide units and better still from 2 to 10 ethylene oxide units.

Use may also be made of the C6-C24 alkyl monoesters of polyglycoside-polycarboxylic acids, such as C6-C24 alkyl polyglycoside-citrates, C6-C24 alkyl polyglycoside-tartrates and C6-C24 alkyl polyglycoside-sulfosuccinates, and salts thereof.

Among the above carboxylic surfactants, mention may be made most particularly of polyoxyalkylenated alkyl(amido) ether carboxylic acids and salts thereof, in particular those comprising from 2 to 50 alkylene oxide and in particular ethylene oxide groups, such as the compounds sold by the company Kao under the name Akypo, The polyoxyalkylenated alkyl (amido)ether carboxylic acids that may be used are preferably chosen from those of formula (1):

$$R_1—(OC_2H_4)_n—OCH_2COOA \quad (1)$$

in which:

R1 represents a linear or branched C6-C24 alkyl or alkenyl radical, an alkyl(C8-C9)phenyl radical, a radical R2CONH—CH2-CH2- with R2 denoting a linear or branched C9-C21 alkyl or alkenyl radical, preferably, R1 is a C8-C20 and preferably C8-C18 alkyl radical, and aryl preferably denotes phenyl, n is an integer or decimal number (average value) ranging from 2 to 24 and preferably from 2 to 10, A denotes H, ammonium, Na, K, Li, Mg or a monoethanolamine or triethanolamine residue.

It is also possible to use mixtures of compounds of formula (1), in particular mixtures of compounds containing different groups R1.

The polyoxyalkylenated alkyl(amido) ether carboxylic acids that are particularly preferred are those of formula (1) in which:

R1 denotes a C12-C14 alkyl, cocoyl, oleyl, nonylphenyl or octylphenyl radical,

A denotes a hydrogen or sodium atom, and n varies from 2 to 20 and preferably from 2 to 10.

Even more preferentially, use is made of compounds of formula (1) in which R denotes a C12 alkyl radical, A denotes a hydrogen or sodium atom and n ranges from 2 to 10.

Preferentially, the carboxylic anionic surfactants are chosen, alone or as a mixture, from:

acylglutamates, especially of C6-C24 or even C12-C20, such as stearoylglutamates, and in particular disodium stearoylglutamate;

acylsarcosinates, especially of C6-C24 or even C12-C20, such as palmitoylsarcosinates, and in particular sodium palmitoylsarcosinate;

acyllactylates, especially of C12-C28 or even C14-C24, such as behenoyllactylates, and in particular sodium behenoyllactylate;

C6-C24 and especially C12-C20 acylglycinates;

(C6-C24)alkyl ether carboxylates and especially (C12-C20)alkyl ether carboxylates;

polyoxyalkylenated ($C_6$-$C_{24}$)alkyl(amido) ether carboxylic acids, in particular those comprising from 2 to 50 ethylene oxide groups;

in particular in the form of alkali metal or alkaline-earth metal, ammonium or amino alcohol salts.

The sulfonate anionic surfactants that may be used comprise at least one sulfonate function (—$SO_3H$ or —$SO_3$—).

They may be chosen from the following compounds: alkylsulfonates, alkylamidesulfonates, alkylarylsulfonates, α-olefinsulfonates, paraffin sulfonates, alkylsulfosuccinates, alkyl ether sulfosuccinates, alkylamidesulfosuccinates, alkylsulfoacetates, N-acyltaurates, acylisethionates; alkylsulfolaurates; and also the salts of these compounds;

the alkyl groups of these compounds comprising from 6 to 30 carbon atoms, especially from 12 to 28, better still from 14 to 24 or even from 16 to 22 carbon atoms; the aryl group preferably denoting a phenyl or benzyl group;

these compounds possibly being polyoxyalkylenated, especially polyoxyethylenated, and then preferably comprising from 1 to 50 ethylene oxide units and better still from 2 to 10 ethylene oxide units.

Preferentially, the sulfonate anionic surfactants are chosen, alone or as a mixture, from:
C6-C24 and especially C12-C20 alkylsulfosuccinates, especially laurylsulfosuccinates;
C6-C24 and especially C12-C20 alkyl ether sulfosuccinates;
(C6-C24)acylisethionates and preferably (C12-C18)acylisethionates,
in particular in the form of alkali metal or alkaline-earth metal, ammonium or amino alcohol salts.

The sulfate anionic surfactants that may be used comprise at least one sulfate function (—OSO$_3$H or —OSO$_3$—).

They may be chosen from the following compounds: alkyl sulfates, alkyl ether sulfates, alkylamido ether sulfates, alkylaryl polyether sulfates, monoglyceride sulfates; and also the salts of these compounds;
the alkyl groups of these compounds comprising from 6 to 30 carbon atoms, especially from 12 to 28, better still from 14 to 24 or even from 16 to 22 carbon atoms; the aryl group preferably denoting a phenyl or benzyl group;
these compounds possibly being polyoxyalkylenated, especially polyoxyethylenated, and then preferably comprising from 1 to 50 ethylene oxide units and better still from 2 to 10 ethylene oxide units.

Preferentially, the sulfate anionic surfactants are chosen, alone or as a mixture, from:
alkyl sulfates, especially of C6-C24 or even C12-C20,
alkyl ether sulfates, especially of C6-C24 or even C12-C20, preferably comprising from 2 to 20 ethylene oxide units;
in particular in the form of alkali metal or alkaline-earth metal, ammonium or amino alcohol salts.

When the anionic surfactant is in salt form, the said salt may be chosen from alkali metal salts, such as the sodium or potassium salt, ammonium salts, amine salts and in particular amino alcohol salts, and alkaline-earth metal salts, such as the magnesium salt.

Examples of amino alcohol salts that may be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts and in particular the sodium or magnesium salts are preferably used.

Preferentially, the anionic surfactants are chosen, alone or as a mixture, from:
C6-C24 and especially C12-C20 alkyl sulfates;
C6-C24 and especially C12-C20 alkyl ether sulfates; preferably comprising from 2 to 20 ethylene oxide units;
C6-C24 and especially C12-C20 alkylsulfosuccinates, especially laurylsulfosuccinates;
C6-C24 and especially C12-C20 alkyl ether sulfosuccinates;
(C6-C24)acylisethionates and preferably (C12-C18)acylisethionates;
C6-C24 and especially C12-C20 acylsarcosinates; especially palmitoylsarcosinates;
(C6-C24)alkyl ether carboxylates, preferably (C12-C20) alkyl ether carboxylates;
polyoxyalkylenated (C6-C24)alkyl(amido) ether carboxylic acids and salts thereof, in particular those comprising from 2 to 50 alkylene oxide and in particular ethylene oxide groups;
C6-C24 and especially C12-C20 acylglutamates;
C6-C24 and especially C12-C20 acylglycinates;
in particular in the form of alkali metal or alkaline-earth metal, ammonium or amino alcohol salts.

It should be noted that the alkyl or acyl radicals of these various compounds preferably comprise from 12 to 20 carbon atoms. Preferably, the aryl radical denotes a phenyl or benzyl group.

Furthermore, the polyoxyalkylenated anionic surfactants preferably comprise from 2 to 50 alkylene oxide groups, in particular ethylene oxide groups.

Preferably, the anionic surfactants of the invention are sulfates, more specifically is chosen from ($C_6$-$C_{30}$)alkyl sulfates, ($C_6$-$C_{30}$)alkyl ether sulfates, ($C_6$-$C_{30}$)alkylamido ether sulfates, alkylaryl polyether sulfates and monoglyceride sulfates, their salts such as alkali salts, such as sodium, and their mixtures.

More preferably the anionic surfactants of the invention are chosen from ($C_6$-$C_{30}$)alkyl sulfates, ($C_6$-$C_{30}$)alkyl ether sulfates, particularly ($C_6$-$C_{30}$)alkyl ether sulfates such as lauryl ether sulfate, their salts, such as sodium lauryl ether sulfate.

ii) Nonionic Surfactants

Among the nonionic surfactants that could be present in the composition according to the invention, mention may be made of alcohols, α-diols and ($C_{1-20}$)alkylphenols, these compounds being polyethoxylated and/or polypropoxylated and/or polyglycerolated, the number of ethylene oxide and/or propylene oxide groups possibly ranging from 1 to 100, and the number of glycerol groups possibly ranging from 2 to 30; or alternatively these compounds comprising at least one fatty chain comprising from 8 to 30 carbon atoms and especially from 16 to 30 carbon atoms.

Mention may also be made of condensates of ethylene oxide and of propylene oxide with fatty alcohols; polyethoxylated fatty amides preferably having from 2 to 30 ethylene oxide units, polyglycerolated fatty amides comprising on average from 1 to 5, and in particular from 1.5 to 4, glycerol groups; ethoxylated fatty acid esters of sorbitan preferably containing from 2 to 40 ethylene oxide units, fatty acid esters of sucrose, polyoxyalkylenated and preferably polyoxyethylenated fatty acid esters containing from 2 to 150 mol of ethylene oxide, including oxyethylenated plant oils, N—(C6-24 alkyl)glucamine derivatives, amine oxides such as (C10-14 alkyl)amine oxides or N—(C10-14 acyl) aminopropylmorpholine oxides.

Mention may also be made of nonionic surfactants of alkyl(poly)glycoside type, represented especially by the following general formula: $R_1O—(R_2O)_t—(G)_v$
in which:
$R_1$ represents a linear or branched alkyl or alkenyl radical comprising 6 to 24 carbon atoms and especially 8 to 18 carbon atoms, or an alkylphenyl radical whose linear or branched alkyl radical comprises 6 to 24 carbon atoms and especially 8 to 18 carbon atoms;
$R_2$ represents an alkylene radical comprising 2 to 4 carbon atoms,
G represents a sugar unit comprising 5 to 6 carbon atoms,
t denotes a value ranging from 0 to 10 and preferably 0 to 4,
v denotes a value ranging from 1 to 15 and preferably 1 to 4.

Preferably, the alkylpolyglycoside surfactants are compounds of the formula described above in which:
- $R_1$ denotes a linear or branched, saturated or unsaturated alkyl radical comprising from 8 to 18 carbon atoms,
- $R_2$ represents an alkylene radical comprising 2 to 4 carbon atoms,
- t denotes a value ranging from 0 to 3 and preferably equal to 0,
- G denotes glucose, fructose or galactose, preferably glucose;
- the degree of polymerization, i.e. the value of v, possibly ranging from 1 to 15 and preferably from 1 to 4; the mean degree of polymerization more particularly being between 1 and 2.

The glucoside bonds between the sugar units are generally of 1-6 or 1-4 type and preferably of 1-4 type. Preferably, the alkyl(poly)glycoside surfactant is an alkyl(poly)glucoside surfactant. C8/C16 alkyl(poly)glycosides 1,4, and especially decyl glucosides and caprylyl/capryl glucosides, are most particularly preferred. Among the commercial products, mention may be made of the products sold by the company COGNIS under the names PLANTAREN® (600 CS/U, 1200 and 2000) or PLANTACARE® (818, 1200 and 2000); the products sold by the company SEPPIC under the names ORAMIX CG 110 and ORAMIX NS 10; the products sold by the company BASF under the name LUTENSOL GD 70, or else the products sold by the company CHEM Y under the name AG10 LK.

Preferably, use is made of C8/C16-alkyl(poly)glycosides 1,4, especially as an aqueous 53% solution, such as those sold by Cognis under the reference Plantacare® 818 UP.

As regards the mono- or polyglycerolated surfactants, they preferably comprise on average from 1 to 30 glycerol groups, more particularly from 1 to 10 glycerol groups and in particular from 1.5 to 5.

The monoglycerolated or polyglycerolated surfactants are preferably chosen from the compounds of the following formulae:

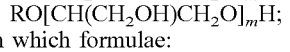

in which formulae:
- R represents a saturated or unsaturated, linear or branched hydrocarbon-based radical comprising from 8 to 40 carbon atoms and preferably from 10 to 30 carbon atoms; R may optionally comprise heteroatoms, for instance oxygen and nitrogen.
- m is an integer between 1 and 30, preferably between 1 and 10 and more particularly from 1.5 to 6.

In particular, R may optionally comprise one or more hydroxyl and/or ether and/or amide groups. R preferably denotes mono- or polyhydroxylated $C_{10}$-$C_{20}$ alkyl, and/or alkenyl radicals.

Use may be made, for example, of the polyglycerolated (3.5 mol) hydroxylauryl ether sold under the name Chimexane® NF from Chimex.

The (poly)ethoxylated fatty alcohols that are suitable for performing the invention are chosen more particularly from alcohols containing from 8 to 30 carbon atoms, and preferably from 12 to 22 carbon atoms.

The (poly)ethoxylated fatty alcohols more particularly contain one or more linear or branched, saturated or unsaturated hydrocarbon-based groups, comprising 8 to 30 carbon atoms, which are optionally substituted, in particular with one or more (in particular 1 to 4) hydroxyl groups. If they are unsaturated, these compounds may comprise one to three conjugated or non-conjugated carbon-carbon double bonds.

The (poly)ethoxylated fatty alcohol(s) preferably have the following formula (II): $R_3$—$(OCH_2CH_2)_c$OH with:
- $R_3$ representing a linear or branched $C_8$-$C_{40}$ alkyl or alkenyl group, preferably $C_8$-$C_{30}$ alkyl or alkenyl group, optionally substituted with one or more hydroxyl groups, and
- c is an integer between 1 and 200 inclusive, preferentially between 2 and 150 and more particularly between 4 and 50, most preferably between 8 and 20.

The (poly)ethoxylated fatty alcohols are more particularly fatty alcohols comprising from 8 to 22 carbon atoms, oxyethylenated with 1 to 30 mol of ethylene oxide (1 to 30 OE). Among these, mention may be made more particularly of lauryl alcohol 2 OE, lauryl alcohol 3 OE, decyl alcohol 3 OE, decyl alcohol 5 OE and oleyl alcohol 20 OE. Mixtures of these (poly)oxyethylenated fatty alcohols may also be used.

Preferentially, the nonionic surfactants are chosen from (C6-C24 alkyl)polyglycosides, and more particularly (C8-C18 alkyl)(poly)glycosides, ethoxylated C8-C30 fatty acid esters of sorbitan, polyethoxylated C8-C30 fatty alcohols and polyoxyethylenated C8-C30 fatty acid esters, these compounds preferably containing from 2 to 150 mol of ethylene oxide, and mixtures thereof.

iii) Amphoteric Surfactants

The amphoteric surfactant(s) that may be used in the present invention may be quaternized secondary or tertiary aliphatic amine derivatives containing at least one anionic group, for instance a carboxylate, sulfonate, sulfate, phosphate or phosphonate group, and in which the aliphatic group or at least one of the aliphatic groups is a linear or branched chain comprising from 8 to 22 carbon atoms. Mention may be made in particular of ($C_8$-$C_{20}$)alkylbetaines, sulfobetaines, ($C_8$-$C_{20}$ alkyl)amido($C_2$-$C_8$ alkyl)betaines and ($C_8$-$C_{20}$ alkyl)amido($C_2$-$C_8$ alkyl)sulfobetaines.

Among the optionally quaternized secondary or tertiary aliphatic amine derivatives that may be used, mention may also be made of the products of respective structures (III) and (IV) below:

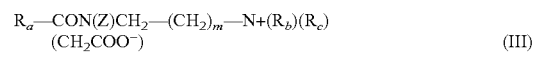

in which:
- $R_a$ represents a $C_{10}$-$C_{30}$ alkyl or alkenyl group derived from an acid $R_a$—COOH preferably present in hydrolysed coconut oil, a heptyl group, a nonyl group or an undecyl group,
- $R_b$ represents a β-hydroxyethyl group,
- $R_c$ represents a carboxymethyl group;
- m is equal to 0, 1 or 2,
- Z represents a hydrogen atom or a hydroxyethyl or carboxymethyl group;

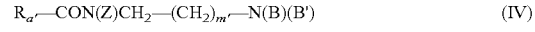

in which:
- B represents —$CH_2CH_2OX'$, with X' representing —$CH_2$—COOH, $CH_2$—COOZ', —$CH_2CH_2$—COOH, —$CH_2CH_2$—COOZ', or a hydrogen atom,
- B' represents —$(CH_2)_z$—Y', with z=1 or 2, and Y' representing —COOH, —COOZ', —$CH_2$—CHOH—$SO_3$H or —$CH_2$—CHOH—$SO_3$Z',
- m' is equal to 0, 1 or 2,
- Z represents a hydrogen atom or a hydroxyethyl or carboxymethyl group,
- Z' represents an ion resulting from an alkali or alkaline-earth metal, such as sodium, potassium or magnesium; an ammonium ion; or an ion resulting from an organic amine and in particular from an amino alcohol, such as monoethanolamine, diethanolamine and triethanolamine, monoisopropanolamine, diisopropanolamine or triisopropanolamine, 2-amino-2-methyl-1-propanol, 2-amino-2-methyl-1,3-propanediol and tris(hydroxymethyl)aminomethane, $R_{a'}$ represents a $C_{10}$-$C_{30}$ alkyl or alkenyl group of an acid $R_aCOOH$ preferably present in hydrolysed linseed oil or coconut oil, an alkyl group, in particular a $C_{17}$ alkyl group, and its iso form, or an unsaturated $C_{17}$ group.

The compounds corresponding to formula (IV) are preferred.

Among the compounds corresponding to formula (IV) in which X' represents an hydrogen atom, mention may be made of compounds classified in the CTFA dictionary, under the names sodium cocoamphoacetate, sodium lauroamphoacetate, sodium caproamphoacetate and sodium capryloamphoacetate.

Other compounds corresponding to formula (IV) are disodium cocoamphodiacetate, disodium lauroamphodiacetate, disodium caproamphodiacetate, disodium capryloamphodiacetate, disodium cocoamphodipropionate, disodium lauroamphodipropionate, disodium caproamphodipropionate, disodium capryloamphodipropionate, lauroamphodipropionic acid and cocoamphodipropionic acid.

Examples that may be mentioned include the cocoamphodiacetate sold by the company Rhodia under the trade name Miranol® C2M Concentrate, the sodium cocoamphoacetate sold under the trade name Miranol Ultra C 32 and the product sold by the company Chimex under the trade name CHIMEXANE HA.

Use may also be made of the compounds of formula (V):

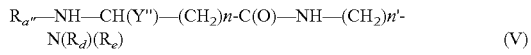

(V)

in which:

$R_{a''}$ represents a $C_{10}$-$C_{30}$ alkyl or alkenyl group of an acid $R_{a''}$—C(O)OH preferably present in hydrolysed linseed oil or coconut oil;

Y" represents the group —C(O)OH, —C(O)OZ", —CH$_2$—CH(OH)—SO$_3$H or the group —CH$_2$—CH(OH)—SO$_3$—Z", with Z" representing a cationic counterion resulting from an alkali metal or alkaline-earth metal, such as sodium, an ammonium ion or an ion resulting from an organic amine;

$R_d$ and $R_e$ represent, independently of each other, a C1-C4 alkyl or hydroxyalkyl radical; and n and n' denote, independently of each other, an integer ranging from 1 to 3.

Among the compounds corresponding to formula (V), mention may in particular be made of the compound classified in the CTFA dictionary under the name sodium diethylaminopropyl cocoaspartamide, such as the one sold by the company Chimex under the name CHIMEXANE HB.

Preferably, the amphoteric surfactants are chosen from (C8-C20)alkylbetaines, (C8-C20)alkylamido(C1-C6)alkylbetaines, (C8-C20)alkylamphoacetates and (C8-C20)alkylamphodiacetates, and mixtures thereof.

Among all the amphoteric surfactants mentioned above, use is preferably made of cocoylamidopropylbetaine, cocoylbetaine and the N-cocoylamidocarboxymethyl glycinate of an alkali metal such as sodium.

Preferably, the composition according to the invention contains one or more anionic surfactants and one or more amphoteric surfactants; more preferably, the composition according to the invention contains one or more anionic surfactants, one or more nonionic surfactants and one or more amphoteric surfactants.

Advantageously, the composition according to the invention may comprise the surfactant(s) in a total quantity ranging of from 4% to 50% by weight, with respect to the weight of the composition, preferably from 6% to 40% by weight, more preferably from 10% to 30% by weight, even more preferably from 12% to 25% by weight, with respect to the weight of the composition.

Advantageously, the composition according to the invention may comprise the anionic surfactant(s) in a quantity ranging of from 4% to 50% by weight, with respect to the weight of the composition, preferably from 6% to 40% by weight, more preferably from 10% to 30% by weight, even more preferably from 12% to 25% by weight, and even more preferably from 12 to 20% by weight, with respect to the weight of the composition.

Advantageously, the composition according to the invention may comprise the nonionic surfactant(s) in a quantity ranging of from 0.01% to 15% by weight, especially ranging from 0.1% to 10% by weight, better still from 0.2% to 8% by weight and preferentially from 0.5% to 5% by weight, relative to the total weight of the composition.

Advantageously, the composition according to the invention may comprise the amphoteric surfactant(s) in a quantity ranging of from 0,1% to 15% by weight, with respect to the weight of the composition, preferably from 0.5% to 10% by weight, more preferably from 1% to 8% by weight, even more preferably from 1,5% to 5% by weight, with respect to the weight of the composition.

B—Silicone-in-Water (or Oil-in-Water) Emulsion

The cosmetic composition according to the invention further comprises an oil-in-water emulsion having $D_{50}$ particle size of less than 350 nm and that comprises:

a silicone mixture comprising (i) a trialkylsilyl terminated dialkylpolysiloxane having a viscosity of from 40,000 to less than 100,000 mPa·s at 25° C. and (ii) an amino silicone having a viscosity of from 1,000 to 15,000 mPa·s at 25° C. and an amine value of from 2 to 10 mg of KOH per gram of amino silicone;

a mixture of emulsifiers comprising one or more nonionic emulsifiers, wherein the mixture of emulsifiers has a HLB value of from 10 to 16; and water.

In the oil-in-water emulsion, or silicone-in-water emulsion, one liquid phase (the dispersed phase) is dispersed in the other liquid phase (the continuous phase); in the present invention, the silicone mixture, or silicone phase, is dispersed in the continuous aqueous phase.

The silicone mixture comprises one or more trialkylsilyl terminated dialkylpolysiloxanes, that are preferably of formula (I): R'$_3$SiO(R'$_2$SiO)$_p$SiR'$_3$ wherein:

R', same or different, is a monovalent hydrocarbon radical having from 1 to 18 carbon atoms, preferably from 1 to 6 carbon atoms, even better from 1 to 3 carbon atoms, more preferably methyl, and p is an integer of from 500 to 2000, preferably of from 1000 to 2000.

The trialkylsilyl terminated (or end-blocked or α,ω-position) dialkylpolysiloxanes according to the invention have a viscosity of from 40,000 to less than 100,000 mPa·s (100,000 excluded) at 25° C., preferably a viscosity of from 40,000 to 70,000 mPa·s at 25° C., more preferably a viscosity of from 51,000 to 70,000 mPa·s at 25° C.

The trialkylsilyl terminated dialkylpolysiloxanes according to the invention are preferably linear but may contain additionally to the R'$_2$SiO$_{2/2}$ units (D-units) in formula (I), RSiO$_{3/2}$ units (T-units) and/or SiO$_{4/2}$ units (Q-units), wherein R', same or different, is a monovalent hydrocarbon radical having from 1 to 18 carbon atoms.

Preferably, R', same or different, are alkyl radicals, preferably C1-C28 alkyl radicals, such as the methyl, ethyl, n-propyl, isopropyl, 1-n-butyl, 2-n-butyl, isobutyl, tert-butyl, n-pentyl, isopentyl, neopentyl and tert-pentyl radicals, hexyl radicals, such as the n-hexyl radical, heptyl radicals such as the n-heptyl radical, octyl radicals such as the n-octyl radical and isooctyl radicals, such as the 2,2,4-trimethylpentyl radical, nonyl radicals, such as the n-nonyl radicals, decyl radicals, such as the n-decyl radical, dodecyl radicals, such as the n-dodecyl radical, and octadecyl radicals, such as the n-octadecyl radical; alkenyl radicals such as the vinyl and ally radical; cycloalkyl radicals, such as the cyclopentyl, cyclohexyl, cycloheptyl and methylcyclohexyl radicals; aryl radicals, such as the phenyl, naphthyl, anthryl and phenanthryl radical; alkaryl radicals, such as the o-, m- and p-tolyl radicals, xylyl radicals and ethylphenyl radicals; and aralkyl radicals such as the benzyl radical and the a- and the b-phenylethyl radical. Most preferred is the methyl radical.

Preferably, the trialkylsilyl terminated dialkylpolysiloxanes are trimethylsilyl terminated PDMS (polydimethylsiloxanes or dimethicones).

The silicone mixture comprises one or more amino silicones, that are preferably of formula (II): XR$_2$Si(OSiAR)$_n$(OSiR$_2$)$_m$OSiR$_2$X
wherein:
  R, same or different, is a monovalent hydrocarbon radical having from 1 to 18 carbon atoms, preferably from 1 to 6 carbon atoms, even better from 1 to 3 carbon atoms, more preferably methyl,
  X, same or different, is R or a hydroxyl (OH) or a C$_1$-C$_6$-alkoxy group; preferably X is R, i.e. a monovalent hydrocarbon radical having from 1 to 18 carbon atoms, preferably from 1 to 6 carbon atoms, even better from 1 to 3 carbon atoms, more preferably methyl, and
  A is an amino radical of the formula —R$^1$—[NR$^2$—R$^3$—]$_x$NR$^2$$_2$, or the protonated amino forms of said amino radical, wherein R$^1$ is a C$_1$-C$_6$-alkylene radical, preferably a radical of the formula —CH$_2$CH$_2$CH$_2$— or —CH$_2$CH(CH$_3$)CH$_2$—, R$^2$, same or different, is a hydrogen atom or a C$_1$-C$_4$-alkyl radical, preferably a hydrogen atom, R$^3$ is a C$_1$-C$_6$-alkylene radical, preferably a radical of the formula —CH$_2$CH$_2$—, and x is 0 or 1;
  m+n is an integer from 50 to about 1000, preferably from 50 to 600.

Preferably, A is an amino radical of the formula —R$^1$—[NR$^2$—R$^3$—]$_x$NR$^2$$_2$, or the protonated amino forms of said amino radical, wherein R$^1$ is —CH$_2$CH$_2$CH$_2$— or —CH$_2$CH(CH$_3$)CH$_2$—, R$^2$ are hydrogen atoms, R$^3$ is —CH$_2$CH$_2$—, and x is 1.

Preferably, R, same or different, are alkyl radicals, preferably C1-C28 alkyl radicals, such as the methyl, ethyl, n-propyl, isopropyl, 1-n-butyl, 2-n-butyl, isobutyl, tert-butyl, n-pentyl, isopentyl, neopentyl and tert-pentyl radicals, hexyl radicals, such as the n-hexyl radical, heptyl radicals such as the n-heptyl radical, octyl radicals such as the n-octyl radical and isooctyl radicals, such as the 2,2,4-trimethylpentyl radical, nonyl radicals, such as the n-nonyl radicals, decyl radicals, such as the n-decyl radical, dodecyl radicals, such as the n-dodecyl radical, and octadecyl radicals, such as the n-octadecyl radical; alkenyl radicals such as the vinyl and ally radical; cycloalkyl radicals, such as the cyclopentyl, cyclohexyl, cycloheptyl and methylcyclohexyl radicals; aryl radicals, such as the phenyl, naphthyl, anthryl and phenanthryl radical; alkaryl radicals, such as the o-, m- and p-tolyl radicals, xylyl radicals and ethylphenyl radicals; and aralkyl radicals such as the benzyl radical and the a- and the b-phenylethyl radical. Most preferred is the methyl radical.

The amino silicones according to the invention have a viscosity of from 1,000 to 15,000 mPa·s at 25° C., preferably of from 1,500 to 15,000 mPa·s.

The amino silicones according to the invention have an amine value of from 2 to 10 mg of KOH per gram of amino silicone, preferably of from 3.5 to 8 mg.

The mole percent of amine functionality is preferably in the range of from about 0.3 to about 8%.

Examples of amino silicones useful in the silicone mixture according to the invention include trialkylsilyl terminated amino silicone.

Most preferably, amino silicones are trimethylsilyl terminated aminoethylaminopropylmethylsiloxane, most preferably trimethylsilyl terminated aminoethylaminopropylmethylsiloxane—dimethylsiloxane copolymers.

The amino radical A can be protonated partially or fully by adding acids to the amino silicone, wherein the salt forms of the amino radical are obtained. Examples of acids are carboxylic acids with 3 to 18 carbon atoms which can be linear or branched, such as formic acid, acetic acid, propionic acid, butyric acid, pivalic acid, sorbic acid, benzoic acid, salicylic acid. The acids are preferably used in amounts of from 0.1 to 2.0 mol per 1 mol of amino radical A in the amino silicone of formula (II).

The silicone mixture preferably comprises (i) one or more trialkylsilyl terminated dialkylpolysiloxanes having a viscosity of from 40,000 to less than 100,000 mPa·s at 25° C. in a quantity of from 70 to 90% by weight, preferably from 75 to 85% by weight and (ii) one or more amino silicones having a viscosity of from 1,000 to 15,000 mPa·s at 25° C. and an amine value of from 2 to 10 mg of KOH per gram of amino silicone, in a quantity of from 10 to 30% by weight, preferably from 15 to 25% by weight, relative to the total weight of the silicone mixture.

The oil-in-water emulsion further comprises a mixture of emulsifiers that comprises one or more nonionic emulsifiers. It could optionally comprise one or more cationic surfactants.

The mixture of emulsifiers has a HLB value from 10 to 16.

The nonionic emulsifiers can be chosen among the nonionic surfactants previously described.

The nonionic emulsifiers could preferably be chosen among ethoxylated aliphatic alcohols, polyoxyethylene surfactants, carboxylic esters, polyethylene glycol esters, sorbitol ester and their ethoxylated derivatives, glycol esters of fatty acids, carboxylic amides, monoalkanolamine condensates, polyoxyethylene fatty acid amides.

Preferably, nonionic emulsifiers are selected from:
  (i) polyoxyalkylene alkyl ethers, especially (poly)ethoxylated fatty alcohols of formula: R$_3$—(OCH$_2$CH$_2$)$_c$OH with:
    R$_3$ representing a linear or branched C$_8$-C$_{40}$ alkyl or alkenyl group, preferably C$_8$-C$_{30}$ alkyl or alkenyl group, optionally substituted with one or more hydroxyl groups, and
    c being an integer between 1 and 200 inclusive, preferentially between 2 and 150 and more particularly between 4 and 50, most preferably between 8 and 20.

The (poly)ethoxylated fatty alcohols are more particularly fatty alcohols comprising from 8 to 22 carbon atoms, oxyethylenated with 1 to 30 mol of ethylene oxide (1 to 30 OE);

(ii) polyoxyalkylene (C8-C32)alkylphenyl ethers, (iii) polyoxyalkylene sorbitan (C8-C32) fatty acid esters, especially polyethoxylated fatty acid esters of sorbitan preferably containing from 2 to 40 ethylene oxide units, most preferably from 2 to 20 ethylene oxide units; preferably polyoxyethylenated sorbitan (C10-C24) fatty acid esters preferably containing from 2 to 40 ethylene oxide units, most preferably from 2 to 20 ethylene oxide units; and (iv) polyoxyethylenated (C8-C32) fatty acid esters containing for example from 2 to 150 mol of ethylene oxide; preferably polyoxyethylenated (C10-C24) fatty acid esters containing for example from 2 to 150 mol of ethylene oxide.

Preferably, the nonionic emulsifiers could be selected from alkyl ether of polyalkyleneglycol and alkyl esters of polyalkyleneglycol; preferably of polyethyleneglycol.

Some useful emulsifiers are:
polyethyleneglycol octyl ether; polyethyleneglycol lauryl ether; polyethyleneglycol tridecyl ether; polyethyleneglycol cetyl ether; polyethyleneglycol stearyl ether; among these, mention may be made more particularly of trideceth-3, trideceth-10 and steareth-6.
polyethyleneglycol nonylphenyl ether; polyethyleneglycol dodecylphenyl ether; polyethyleneglycol cetylphenyl ether; polyethyleneglycol stearylphenyl ether;
polyethyleneglycol sorbitan monostearate, polyethyleneglycol sorbitan monooleate.
polyethyleneglycol stearate, and especially PEG 100 stearate.

Most preferably, the nonionic emulsifiers are chosen among steareth-6, Peg100 stearate, trideceth-3 and trideceth-10 and their mixture; preferably, all these emulsifiers are present in the mixture of emulsifiers.

The mixture of emulsifiers could comprise one or more cationic emulsifiers that could be selected among tetraalkylammonium halides, tetraarylammonium halides, tetraalkylarylammonium halides, and their salts; quaternary ammonium compounds including salts; preferably, the cationic emulsifiers could be chosen among cetrimonium halides or behentrimonium halides, such as chloride.

The oil-in-water emulsion preferably comprises the mixture of emulsifiers in a total amount of from 5 to 15% by weight, preferably of from 8 to 15% by weight, most preferably of from 10 to 12% by weight, relative to the total weight of the emulsion. The oil-in-water emulsion preferably comprises nonionic emulsifiers in a total amount of from 5 to 15% by weight, preferably of from 8 to 15% by weight, most preferably of from 10 to 12% by weight, relative to the total weight of the emulsion. The oil-in-water emulsion preferably comprises cationic emulsifiers, when present, in a total amount of from 0.5 to 1,5% by weight, relative to the total weight of the emulsion.

The oil-in-water emulsion preferably comprises the silicone mixture in a total amount of from 40 to 60% by weight, preferably of from 45 to 55% by weight, relative to the total weight of the emulsion.

The oil-in-water emulsion preferably comprises the trialkylsilyl terminated dialkylpolysiloxane(s) in a total amount of from 35 to 45% by weight, preferably of from 38-42% by weight, relative to the total weight of the emulsion.

The oil-in-water emulsion preferably comprises the amino silicone(s) in a total amount of from 5 to 15% by weight, preferably of from 8-12% by weight, relative to the total weight of the emulsion.

The oil-in-water emulsion comprises water preferably in an amount of from 25 to 50% by weight, preferably of from 30 to 45% by weight, most preferably of from 35 to 42% by weight, relative to the total weight of the emulsion.

The oil-in-water emulsion could additionally comprise a biocide, such as phenoxyethanol, that could be present in the emulsion in a quantity of from 0.5 to 1% by weight, relative to the total weight of the emulsion.

A method of preparation of the oil-in-water emulsion preferably comprises:
  a step of mixing one or more trialkylsilyl terminated dialkylpolysiloxanes of viscosity of from 40,000 to less than 100,000 mPa·s at 25° C. and one or more amino silicones of viscosity of from 1,000 to 15,000 mPa·s at 25° C. and an amine value of from 2 to 10 mg of KOH per gram of amino silicone, at a temperature of from 15° C. to 40° C., preferably at 25° C., to obtain a mixed silicone fluid, then
  a step of adding a mixture of emulsifiers comprising one or more nonionic emulsifiers, wherein the mixture of emulsifiers has a HLB value from 10 to 16, to the mixed silicone fluid to obtain a silicone-emulsifier-mixture, then
  a step of homogenizing the silicone-emulsifier-mixture followed by
  a step of adding, preferably step-wise, water, preferably demineralized water, to obtain an oil-in-water emulsion having $D_{50}$ particle size of less than 350 nm.

The method of preparation of the oil-in-water emulsion could further comprise an additional step of adding a biocide. Biocide could be added for preserving the emulsion against microbial contamination. The biocide could be added at the level of for preserving emulsion against microbial contamination and obtaining the said emulsion. The quantity of the biocide depends on the type of biocide and as recommended by the manufacturer.

The preparation of the mixture of emulsifiers could be made by mixing one or more nonionic emulsifiers.

The pH of the oil-in-water emulsion after neutralization (i.e. after addition of the biocide) is preferably of from 4 to 6.

The oil-in-water emulsion has $D_{50}$ particle size of less than 350 nm, preferably of from 100 to 300 nm, more preferably from 150 to 250 nm, most preferably from 160 to 200 nm. It corresponds to the average hydrodynamic particle diameter. The D50 particle size is expressed in volume. The $D_{50}$ particle size could be measured by using a device ZetaSizer from Malvern, UK, model Nano-ZS, which is based on the Photon Correlation Spectroscopy (PCS) method.

Particle Size Measurement

Emulsion particle size is measured by using a device ZetaSizer from Malvern, UK, model Nano-ZS which is based on the Photon Correlation Spectroscopy (PCS) method. The $D_{50}$ value of particle size (average hydrodynamic particle diameter) is measured, wherein the evaluating algorithm is "cumulants analysis".

Take 0.5 g of the emulsion sample in a 250 ml beaker, 100 ml of demineralized water is poured into it and then mixed properly to get the sample test solution. The sample test solution is poured in the cuvette cell and is put into the slot of the instrument to measure the particle size of the emulsion. $D_{50}$ is defined as the value of the particle diameter at 50% in the cumulative distribution. For example, if $D_{50}$=170 nm, then 50% of the particles in the sample are larger than 170 nm, and 50% smaller than 170 nm or about 50% by volume of all droplets in said emulsion is 170 nm.

Viscosity Measurement

The viscosity, especially of the silicones or of the emulsion, is measured at 25° C. For viscosities between 1000 to 40,000 mPa·s at 25° C.: the viscosity could be measured with an Anton Paar Rheometer; model MCR101, geometry single gap cylinder: CC27 spindle and shear rate of 1 $s^{-1}$ for 2 minutes, at 25° C.

For viscosities between 40,000 to 100,000 mPa·s at 25° C.: the viscosity could be measured with an Anton Paar Rheometer; model MCR101, 25-6 cone (Cone-plate geometry: 25 mm dia./6° cone); the "Zero gap" setting being made and with a shear rate of 1 $s^{-1}$ for 2 minutes, at 25° C.

Three measurements are made for each sample and the viscosity value is taken at 60 secs. MCR Rheometer Series products work as per USP (US Pharmacopeia Convention) 912—Rotational Rheometer methods.

Amine Value Measurement

The amine value is determined by acid-base titration using a potentiometer [Make: Veego; Model: VPT-MG]. 0.6 g of sample is taken in a 500 ml beaker and a toluene-butanol 1:1 mixture is added and stirred to mix the sample thoroughly; then the sample solution is titrated with a 0.1(N) HCl solution. A determination of the blank value with the toluene-butanol 1:1 mixture is also done. The calculation of the amine value is done by the above mentioned potentiometer.

The amine value is calculated according to the formula:
$56.11 \times (V-V_{Blank}) \times N/W$ mg KOH/g of sample,
where V=Volume of HCl required in ml, $V_{Blank}$=Volume of HCl for blank value (without sample) with the toluene-butanol 1:1 mixture in ml; N=Normality of HCl, i.e. 0.1 N, W=weight of the sample taken in gram.

HLB Value

The term HLB is well known to those skilled in the art, and denotes the hydrophilic/lipophilic balance of a surfactant or emulsifier. In the present invention, HLB values refer to the values at 25° C.

The HLB can be measured by experimental determination or can be calculated.

Calculation of HLB value of nonionic surfactans is calculated according to the equation: HLB=(E+P)/5, with E being the weight percentage of oxyethylene-content and P being the weight percentage of polyhydric alcohol content, described in to the publication Griffin, J. Soc. Cosm. Chem. 1954 (vol. 5, n°4), pp. 249-256.

It can also experimentally be determined according to the book of F. Puisieux and M. Seiller, entitled "Galenica 5: Les systèmes disperses—Tome I—Agents de surface et émulsions—Chapitre IV—Notions de HLB et de HLB critique, pp. 153-194—paragraph 1.1.2. Determination de HLB par voie experimentale [Experimental determination of HLB], pp. 164-180".

The calculated HLB is the preferred HLB values that should be taken into account.

Said calculated HLB could be defined as being the following:

"calculated HLB=20×molar mass of the hydrophilic part/ total molar mass."

For an oxyethylenated fatty alcohol, the hydrophilic part corresponds to the oxyethylene units condensed onto the fatty alcohol and the "calculated HLB" then corresponds to the "Griffin HLB" as defined hereabove.

For an ester or an amide, the hydrophilic part is naturally defined as being beyond the carbonyl group, starting from the fatty chain(s).

For ionic surfactants/emulsifiers, the HLB value of individual surfactant/emulsifier can be calculated applying the Davies formula as described in Davies JT (1957), "A quantitative kinetic theory of emulsion type, I. Physical chemistry of the emulsifying agent", Gas/Liquid and Liquid/Liquid Interface (Proceedings of the International Congress of Surface Activity): 426-438.

According to the formula, the HLB is derived by summing the hydrophilic/hydrophobic contribution afforded by the structural components of the emulsifier: HLB=(hydrophilic groups numbers)−n(group number per CH2 group)+7.

Approximate HLB values for some cationic emulsifiers are given in Table IV, in "Cationic emulsifiers in cosmetics", GODFREY, J. Soc. Cosmetic Chemists (1966) 17, pp 17-27.

When two emulsifiers A and B of known HLB are blended for use, the $HLB_{Mix}$ is said to be the required HLB for the mixture. This is expressed by the equation $(W_A HLB_A + W_B HLB_B)/(W_A + W_B) = HLB_{Mix}$, where $W_A$=the amount (weight) of the first emulsifier (A) used, and WB=the amount (weight) of the second emulsifier (B); $HLB_A$, $HLB_B$=the assigned HLB values for emulsifiers A and B; $HLB_{Mix}$=the HLB of the mixture.

Advantageously, the composition according to the invention may comprise the oil-in-water emulsion in a quantity ranging of from 0.1% to 15% by weight, preferably from 0.5% to 10% by weight, more preferably from 1% to 8% by weight, even more preferably from 1,5% to 5% by weight, with respect to the total weight of the composition.

C—Others Ingredients

The composition according to the present invention may further comprise one or more cationic polymers.

The term "cationic polymer" means any polymer comprising cationic groups and/or groups that can be ionized to cationic groups. Preferably, the cationic polymer is hydrophilic or amphiphilic. The preferred cationic polymers are chosen from those that contain units comprising primary, secondary, tertiary and/or quaternary amine groups that may either form part of the main polymer chain or may be borne by a side substituent directly connected thereto.

The cationic polymers that may be used preferably have a weight-average molar mass (Mw) of between 500 and $5 \times 10^6$ approximately and preferably between $10^3$ and $3 \times 10^6$ approximately.

Among the cationic polymers, mention may be made more particularly of:

(1) homopolymers or copolymers derived from acrylic or methacrylic esters or amides and comprising at least one of the units of the following formulae:

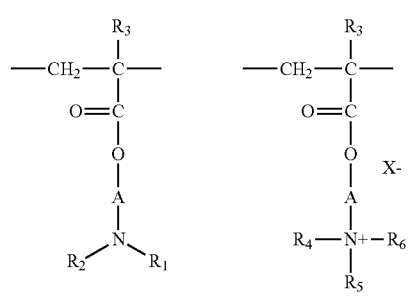

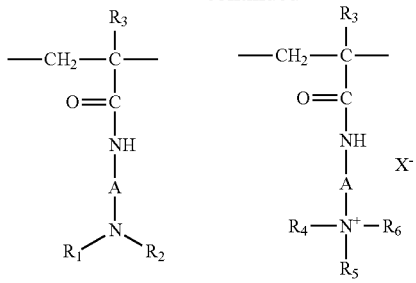

in which:
R3, which may be identical or different, denote a hydrogen atom or a CH$_3$ radical;
A, which may be identical or different, represent a linear or branched divalent alkyl group of 1 to 6 carbon atoms, preferably 2 or 3 carbon atoms, or a hydroxyalkyl group of 1 to 4 carbon atoms;
R4, R5 and R6, which may be identical or different, represent an alkyl group containing from 1 to 18 carbon atoms or a benzyl radical, preferably an alkyl group containing from 1 to 6 carbon atoms;
R1 and R2, which may be identical or different, represent a hydrogen atom or an alkyl group containing from 1 to 6 carbon atoms, preferably methyl or ethyl;
X denotes an anion derived from an inorganic or organic acid, such as a methosulfate anion or a halide such as chloride or bromide.

The copolymers of family (1) may also contain one or more units derived from comonomers that may be selected from the family of acrylamides, methacrylamides, diacetone acrylamides, acrylamides and methacrylamides substituted on the nitrogen with lower (C$_1$-C$_4$) alkyls, acrylic or methacrylic acids or esters thereof, vinyllactams such as vinylpyrrolidone or vinylcaprolactam, and vinyl esters.

Among these copolymers of family (1), mention may be made of:
copolymers of acrylamide and of dimethylaminoethyl methacrylate quaternized with dimethyl sulfate or with a dimethyl halide, such as the product sold under the name HERCOFLOC by the company Hercules,
copolymers of acrylamide and of methacryloyloxyethyltrimethylammonium chloride, such as those sold under the name BINA QUAT P 100 by the company Ciba Geigy,
copolymers of acrylamide and of methacryloyloxyethyltrimethylammonium methosulfate, such as the product sold under the name RETEN by the company Hercules,
quaternized or non-quaternized vinylpyrrolidone/dialkylaminoalkyl acrylate or methacrylate copolymers, such as the products sold under the names GAFQUAT by the company ISP, for instance GAFQUAT 734 or GAFQUAT 755, or alternatively the products known as COPOLYMER 845, 958 and 937.
dimethylaminoethyl methacrylate/vinylcaprolactam/vinylpyrrolidone terpolymers, such as the product sold under the name GAFFIX VC 713 by the company ISP,
vinylpyrrolidone/methacrylamidopropyldimethylamine copolymers, such as those sold under the name STYLEZE CC 10 by ISP,
quaternized vinylpyrrolidone/dimethylaminopropylmethacrylamide copolymers such as the product sold under the name GAFQUAT HS 100 by the company ISP,
preferably crosslinked polymers of methacryloyloxy(C$_1$-C$_4$)alkyltri(C$_1$-C$_4$)alkylammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homopolymerization or copolymerization being followed by crosslinking with an olefinically unsaturated compound, more particularly methylenebisacrylamide. A crosslinked acrylamide/methacryloyloxy ethyltrimethylammonium chloride copolymer (20/80 by weight) in the form of a dispersion containing 50% by weight of the said copolymer in mineral oil may be used more particularly. This dispersion is sold under the name SALCARE® SC 92 by the company BASF. A crosslinked methacryloyloxyethyltrimethylammonium chloride homopolymer containing about 50% by weight of the homopolymer in mineral oil or in a liquid ester can also be used. These dispersions are sold under the names SALCARE® SC 95 and SALCARE® SC 96 by the company BASF.

(2) Cationic polysaccharides, especially cationic celluloses and galactomannan gums. Among the cationic polysaccharides, mention may be made more particularly of cellulose ether derivatives comprising quaternary ammonium groups, cationic cellulose copolymers or cellulose derivatives grafted with a water-soluble quaternary ammonium monomer and cationic galactomannan gums.

The cellulose ether derivatives comprising quaternary ammonium groups are especially described in French patent 1 492 597, and mention may be made of the polymers sold under the name UCARE POLYMER "JR" (JR 400 LT, JR 125 and JR 30M) or "LR" (LR 400 or LR 30M) by the company Amerchol. These polymers are also defined in the CTFA dictionary as quaternary ammoniums of hydroxyethylcellulose that have reacted with an epoxide substituted with a trimethylammonium group.

Cationic cellulose copolymers or cellulose derivatives grafted with a water-soluble quaternary ammonium monomer are described especially in U.S. Pat. No. 4,131,576, and mention may be made of hydroxyalkylcelluloses, for instance hydroxymethyl-, hydroxyethyl- or hydroxypropylcelluloses grafted, in particular, with a methacryloylethyltrimethylammonium, methacrylamidopropyltrimethylammonium or dimethyldiallylammonium salt. The commercial products corresponding to this definition are more particularly the products sold under the names CELQUAT L 200 and CELQUAT H 100 by the company National Starch.

The cationic galactomannan gums are described more particularly in U.S. Pat. Nos. 3.589,578 and 4,031,307, and mention may be made of guar gums comprising cationic trialkylammonium groups. Use is made, for example, of guar gums modified with a 2,3-epoxypropyltrimethylammonium salt (for example, chloride). Such products are especially sold under the names JAGUAR C13 S, JAGUAR C 15, JAGUAR C 17 or JAGUAR C162 by the company Rhodia.

(3) Polymers formed from piperazinyl units and divalent alkylene or hydroxyalkylene radicals containing straight or branched chains, optionally interrupted with oxygen, sulfur or nitrogen atoms or with aromatic or heterocyclic rings, and also the oxidation and/or quaternization products of these polymers.

(4) Water-soluble polyamino amides prepared in particular by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyamino amide; these polyamino amides can be alkylated or, if they comprise one or more tertiary amine functions, they can be quaternized.

(5) Polyamino amide derivatives resulting from the condensation of polyalkylene polyamines with polycarboxylic acids followed by alkylation with bifunctional agents. Mention may be made, for example, of adipic acid/dialkylaminohydroxyalkyldialkylenetriamine polymers in which the alkyl radical comprises from 1 to 4 carbon atoms and preferably denotes methyl, ethyl or propyl. Among these derivatives, mention may be made more particularly of the adipic acid/dimethylaminohydroxypropyl/diethylenetriamine polymers sold under the name CARTARETINE F, F4 or F8 by the company Sandoz.

(6) Polymers obtained by reacting a polyalkylene polyamine comprising two primary amine groups and at least one secondary amine group with a dicarboxylic acid chosen from diglycolic acid and saturated aliphatic dicarboxylic acids containing from 3 to 8 carbon atoms; the mole ratio between the polyalkylene polyamine and the dicarboxylic acid preferably being between 0.8:1 and 1.4:1; the resulting polyamino amide being reacted with epichlorohydrin in a mole ratio of epichlorohydrin relative to the secondary amine group of the polyamino amide preferably of between 0.5:1 and 1.8:1. Polymers of this type are sold in particular under the name HERCOSETT 57 by the company Hercules Inc. or alternatively under the name PD 170 or DELSETTE 101 by the company Hercules in the case of the adipic acid/epoxypropyl/diethylenetriamine copolymer.

(7) Cyclopolymers of alkyldiallylamine or of dialkyldiallylammonium, such as the homopolymers or copolymers containing, as main constituent of the chain, units corresponding to formula (I) or (II):

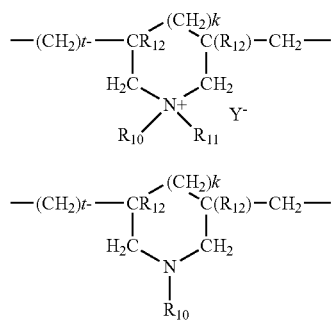

in which:
k and t are equal to 0 or 1, the sum k+t being equal to 1;
R12 denotes a hydrogen atom or a methyl radical;
R10 and R11, independently of each other, denote a C1-06 alkyl group, a hydroxyl(C1-05)alkyl group, a C1-C4 amidoalkyl group; or alternatively R10 and R11 may denote, together with the nitrogen atom to which they are attached, an heterocyclic group such as piperidinyl or morpholinyl; R10 and R11, independently of each other, preferably denote a C1-C4 alkyl group;
Y⁻ is an anion such as bromide, chloride, acetate, borate, citrate, tartrate, bisulfate, bisulfite, sulfate or phosphate.

Mention may be made more particularly of the dimethyldiallylammonium salt (for example chloride) homopolymer sold for example under the name MERQUAT 100 by the company Nalco, and the copolymers of diallyldimethylammonium salts (for example chloride) and of acrylamide, sold especially under the name MERQUAT 550 or MERQUAT 7SPR.

(8) Quaternary diammonium polymers comprising repeating units of formula:

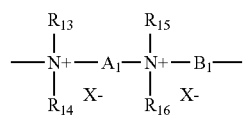

(III)

in which:
R13, R14, R15 and R16, which may be identical or different, represent aliphatic, alicyclic or arylaliphatic radicals comprising from 1 to 20 carbon atoms, or C1-C12 hydroxyalkylaliphatic radicals,
or else R13, R14, R15 and R16, together or separately, constitute, with the nitrogen atoms to which they are attached, heterocycles optionally comprising a second non-nitrogen heteroatom,
or else R13, R14, R15 and R16 represent a linear or branched $C_1$-$C_6$ alkyl radical substituted with a nitrile, ester, acyl, amide or —CO—O—R17-D or —CO—NH—R17-D group in which R17 is an alkylene and D is a quaternary ammonium group;
A1 and B1 represent divalent polymethylene groups comprising from 2 to 20 carbon atoms, linear or branched, saturated or unsaturated, and which may contain, linked to or intercalated in the main chain, one or more aromatic rings or one or more oxygen or sulfur atoms or sulfoxide, sulfone, disulfide, amino, alkylamino, hydroxyl, quaternary ammonium, ureido, amide or ester groups, and
X⁻ denotes an anion derived from an inorganic or organic acid; it being understood that A1, R13 and R15 can form, with the two nitrogen atoms to which they are attached, a piperazine ring;
in addition, if A1 denotes a linear or branched, saturated or unsaturated alkylene or hydroxyalkylene radical, B1 may also denote a group $(CH_2)_n$—CO-D-OC—$(CH_2)_p$— wherein n and p, which may be identical or different, denote an integer from 2 to 20, and wherein D denotes:
a) a glycol residue of formula —O—Z—O—, in which Z denotes a linear or branched hydrocarbon-based radical, or a group corresponding to one of the following formulae: —$(CH_2$—$CH_2$—O$)_x$—$CH_2$—$CH_2$— and —[$CH_2$—$CH(CH_3)$—O$]_y$—$CH_2$—$CH(CH_3)$—, where x and y denote an integer from 1 to 4, representing a defined and unique degree of polymerization or any number from 1 to 4 representing an average degree of polymerization;
b) a bis-secondary diamine residue such as a piperazine derivative;
c) a bis-primary diamine residue of formula: —NH—Y—NH—, where Y denotes a linear or branched hydrocarbon-based radical, or else the divalent radical —CH$_2$—CH$_2$—S—S—CH$_2$—CH$_2$—;

d) a ureylene group of formula: —NH—CO—NH—;

Preferably, X$^-$ is an anion such as chloride or bromide.

These polymers have a number-average molar mass (Mn) generally of between 1000 and 100 000.

Mention may be made more particularly of polymers that are composed of repeating units corresponding to the formula:

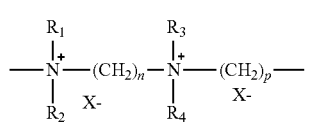

in which R1, R2, R3 and R4, which may be identical or different, denote an alkyl or hydroxyalkyl radical containing from 1 to 4 carbon atoms, n and p are integers ranging from 2 to 20, and X$^-$ is an anion derived from an organic or mineral acid.

A particularly preferred compound of formula (IV) is that for which R1, R2, R3 and R4 represent a methyl radical and n=3, p=6 and X=Cl, known as Hexadimethrine chloride according to the INCI (CTFA) nomenclature.

(9) Polyquaternary ammonium polymers comprising units of formula (V):

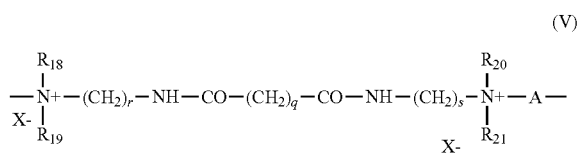

in which:

R18, R19, R20 and R21, which may be identical or different, represent a hydrogen atom or a methyl, ethyl, propyl, β-hydroxyethyl, β-hydroxypropyl or —CH$_2$CH$_2$(OCH$_2$CH$_2$)$_p$OH group, in which p is equal to 0 or to an integer between 1 and 6, with the proviso that R18, R19, R20 and R21 do not simultaneously represent a hydrogen atom, r and s, which may be identical or different, are integers between 1 and 6, q is equal to 0 or to an integer between 1 and 34, X— denotes an anion such as a halide, A denotes a dihalide radical or preferably represents —CH$_2$—CH$_2$—O—CH$_2$—CH$_2$—.

Examples that may be mentioned include the products Mirapol® A15, Mirapol® AD1, Mirapol® AZ1 and Mirapol® 175 sold by the company Miranol.

(10) Quaternary polymers of vinylpyrrolidone and of vinylimidazole, for instance the products sold under the names Luviquat® FC 905, FC 550 and FC 370 by the company BASF.

(11) Polyamines such as Polyquart® H sold by Cognis, referred to under the name Polyethylene glycol (15) tallow polyamine in the CTFA dictionary.

(12) Polymers comprising in their structure:

(a) one or more units corresponding to formula (A) below:

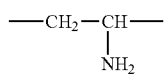

(b) optionally, one or more units corresponding to formula (B) below:

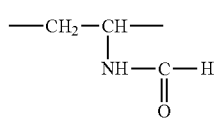

In other words, these polymers may be chosen especially from homopolymers or copolymers comprising one or more units derived from vinylamine and optionally one or more units derived from vinylformamide.

Preferably, these cationic polymers are chosen from polymers comprising, in their structure, from 5 mol % to 100 mol % of units corresponding to formula (A) and from 0 to 95 mol % of units corresponding to formula (B), preferentially from 10 mol % to 100 mol % of units corresponding to formula (A) and from 0 to 90 mol % of units corresponding to formula (B).

These polymers may be obtained, for example, by partial hydrolysis of polyvinylformamide. This hydrolysis may be performed in an acidic or basic medium.

The weight-average molecular mass of the said polymer, measured by light scattering, may range from 1000 to 3 000 000 g/mol, preferably from 10 000 to 1 000 000 g/mol and more particularly from 100 000 to 500 000 g/mol.

The polymers comprising units of formula (A) and optionally units of formula (B) are sold especially under the name Lupamin by the company BASF, for instance, and in a non-limiting manner, the products sold under the names Lupamin 9095, Lupamin 5095, Lupamin 1095, Lupamin 9030 (or Luviquat 9030) and Lupamin 9010.

Other cationic polymers that may be used in the context of the invention are cationic proteins or cationic protein hydrolysates, polyalkyleneimines, in particular polyethyleneimines, polymers comprising vinylpyridine or vinylpyridinium units, condensates of polyamines and of epichlorohydrin, quaternary polyureylenes and chitin derivatives.

Preferably, the cationic polymers are chosen from the polymers of families (1), (2), (7) and (10) mentioned above.

Among the cationic polymers mentioned above, the ones that may preferably be used are cationic polysaccharides, especially cationic celluloses and galactomannan gums, and in particular quaternary cellulose ether derivatives such as the products sold under the name "JR 400" by the company Amerchol, cationic cyclopolymers, in particular dimethyldiallylammonium salt (for example chloride) homopolymers or copolymers, sold under the names Merquat 100, Merquat 550 and Merquat S by the company Nalco, quaternary polymers of vinylpyrrolidone and of vinylimidazole, optionally crosslinked homopolymers or copolymers of methacryloyloxy(C$_1$-C$_4$)alkyltri(C$_1$-C$_4$)alkylammonium salts, and mixtures thereof.

The composition according to the invention may comprise cationic polymer(s) in an amount of between 0.01% and 5% by weight, especially from 0.05% to 3% by weight and preferentially from 0.1% to 2% by weight, relative to the total weight of the composition.

The composition according to the present invention may further comprise one or more oxyethylenated polymers.

The oxyethylenated polymers that may be used in the composition of the invention are preferably those with a molecular weight (Mw) calculated by weight of greater than or equal to 300 000, preferably ranging from 400 000 to $4.10^6$ and better still from 500 000 to $2.10^6$.

The oxyethylenated polymer is preferably a compound of formula (A):

$$H(OCH_2CH_2)_nOH \quad (A)$$

in which n is an integer ranging from 7000 to 90 000, preferably from 10 000 to 75 000, more preferably from 25 000 to 65 000, even more preferably from 35 000 to 55 000.

As oxyethylenated polymer preferably used in the composition of the invention, mention may be made especially of PEG 14M (formula (A) in which n is 14 000) such as the product sold under the name Polyox WSR 205 by the company Amerchol, PEG-45M (formula (A) in which n is 45 000) such as the product sold under the name Polyox WSR N-60 K by the company Amerchol, and mixtures thereof.

The oxyethylenated polymer is preferably present in the composition of the invention in an amount ranging from 0,001% to 5% by weight and better still from 0,005% to 3% by weight, and even more preferably from 0,01% to 1% by weight, relative to the total weight of the composition.

The cosmetic composition of the present invention may comprise water, for example in a quantity of from 40 to 99% by weight, preferably from 50 to 98% by weight, most preferably from 55 to 95% by weight, relative to the total weight of the composition.

The cosmetic composition according to the present invention may further comprise one or more additive(s) other than the compounds of the invention.

As additives that may be used in accordance with the invention, mention may be made of fatty substances, anionic, nonionic or amphoteric polymers or mixtures thereof, cationic surfactants, antidandruff agents, anti-seborrhoea agents, agents for preventing hair loss and/or for promoting hair regrowth, vitamins and provitamins including panthenol, sunscreens, mineral or organic pigments, sequestrants, plasticizers, solubilizers, acidifying agents, mineral or organic thickeners, especially polymeric thickeners, opacifiers, pearlescent or nacreous agents, antioxidants, hydroxyacids, fragrances and preserving agents.

Needless to say, a person skilled in the art will take care to select these optional additives such that the advantageous properties intrinsically associated with the composition according to the invention are not, or are not substantially, adversely affected by the envisaged addition(s).

The composition according to the invention may take the form of thickened liquid, creams or gel, They may also take the form of lotions to be rinsed.

The composition according to the invention is a hair composition, preferably it is a hair shampoo composition.

Another subject of the present invention is a process for the cosmetic treatment of hair, preferably for washing and/or conditioning hair, comprising the steps of applying to the hair, preferably in a wet state, the composition described above, and optionally rinsing them with water after an optional leave-on time.

The leave-on time of the composition on hair may range from a few seconds to 15 minutes, better still from 5 seconds to 10 minutes and even better still from 10 seconds to 5 minutes.

The composition may be applied to wet or dry hair.

The examples that follow serve to illustrate the invention without, however, being limiting in nature.

The stability of the emulsion is determined after 3 months of storage at 45° C.; the stability is determined by no change in property of the emulsion; if the property changes, or if the oil and the aqueous phases separate, the emulsion is said to be unstable.

EXAMPLE 1: PREPARATION OF THE OIL-IN-WATER EMULSION

Transfer 450 g of amino silicone fluid (trimethylsilyl terminated aminoethylaminopropylmethylsiloxane—dimethylsiloxane copolymer with amine value of 7,2 mg of KOH/gm sample, and a viscosity of 5600 mPa·s at 25° C.) in emulsion tank. Start stirring and under stirring condition transfer 1800 g of trimethylsilyl terminated dimethylsiloxane polymer fluid of viscosity 61,500 mPa·s at 25° C. in the same tank. Mix both the fluids for 2 hours at room temperature.

In a separate tank, transfer 49 g of steareth-6, 62 g of PEG100 stearate and heat to 60° C. Maintain the temperature till both emulsifiers become liquid. Then add 31 g of trideceth-3 and 350 g of trideceth-10 (80% of active matter). This nonionic emulsifiers mixture has an HLB value=11.25.

Then add 80 g water and 6.2 g glacial acetic acid in the tank and start mixing. Continue mixing till whole mass become a creamy paste. Whole paste is transfer to emulsion tank. Homogenize for 30 minutes at room temperature. Add 79.6 g demineralized water and homogenize for 60 minutes. Add 72.7 g demineralized water and homogenize for 50 minutes. Add 197.4 g demineralized water and homogenize for 5 minutes. Add 294.3 g demineralized water and homogenize for 5 minutes. Add 180 g demineralized water and homogenize for 5 minutes. Add 180 g demineralized water and homogenize for 5 minutes. Add 197.4 g demineralized water and homogenize for 5 minutes. Add 197.4 g demineralized water and homogenize for 3 minutes. Add 228.5 g demineralized water and homogenize for 3 minutes. Lastly add 40.5 g 2-phenoxyethanol as a biocide and homogenize for 3 minutes.

An stable oil-in-water emulsion having $D_{50}$ particle size of 170 nm is obtained.

EXAMPLE 2: HAIR COMPOSITION

The following composition is prepared from the ingredients indicated in the table below, in which the amounts are given as mass percentages of active material relative to the total weight of the composition (% AM=% active matter).

| Ingredient | % by weight |
| --- | --- |
| Sodium laureth sulfate (1 OE) | 14% AM |
| Cocoylamidopropyl betaine | 1.5% AM |
| Guar hydroxylpropyltrimonium chloride | 0.25% |
| Carbomer | 0.17% |
| Oil-in-water emulsion from example 1 | 3.6% |
| Glycerol | 0.5% |
| PEG-45M (Polyox WSR N 60 K from Dow Chemical) | 0.03% AM |
| Glycol distearate | 1.6% |
| Hexylene glycol | 0.4% |
| NaCl | 1% |
| Fragrance, preservatives | qs |
| Water | qsp 100% |

The composition could be used as a shampoo; it has a pleasant pearlescent appearance and provides good conditioning effects. The foaming properties (foam quality and quantity) are also very good.

The composition is then applied on hair strands. The amount of silicones deposited on the hair is measured after one application. The composition is able to deposit 723 µg of silicone per gram of hair.

The quantity of silicones deposited on the hair is determined by measuring silicium levels using X-ray fluorescence (RC-ANA-MET-1248). Spectrochemical analysis by wavelength dispersive x-ray fluorescence (WDXRF) is based on radiation emissions (spectral lines) characteristic of the chemical element, produced by the impact of high energy photons dispensed by an X-ray tube. Analysis of this fluorescent radiation is performed by counting the number of photons. In this case, i.e. WDXRF, the method consists in separating the photons before counting them using crystal diffraction and positioning the detector at a given wavelength (proportional gas flow counter or a scintillator). The lock to be analysed is prepared by cutting the hair finely with a pair of hairdressing scissors. The "finely cut" hair thus obtained is then placed in the cassette for analysis.

The type of hair (natural or sensitised) does not influence the results.

Instrument: WDXRF Optim'x Thermofisher (Wavelength Dispersion) from Thermo

Characteristics and Operational Parameters:
H 126 cm, W 88 cm, D 82 cm, weight-260 kg
Gas Flow Helium—Argon/Methane (90/10)
X-ray tube (Rh), Cristal PET and detector FPC
Tension 25 kv-2 mA
3 measurements/sample=60 s/measurement
minimum sample size 250 mg (2 mm pieces)
Key Performance Parameters:
Accuracy: 206 ppm—88%; 790 ppm—101%; 1925 ppm—100%
Sensitivity: 80 ppm of Si (LOQ).

EXAMPLE 3: INFLUENCE OF THE HLB 3 oil-in-water emulsions have been prepared as follows:
Step 1: Same for the 3 Emulsions
Transfer 450 g of amino silicone fluid (trimethylsilyl terminated aminoethylaminopropylmethylsiloxane—dimethylsiloxane copolymer with amine value of 7,2 mg of KOH/gm sample, and a viscosity of 5600 mPa·s at 25° C.) in emulsion tank. Start stirring and under stirring condition transfer 1800 g of trimethylsilyl terminated dimethylsiloxane polymer fluid of viscosity 61,500 mPa·s at 25° C. in the same tank.

Mix both the fluids for 2 hours at room temperature.
Step 2:
For emulsion A according to the invention:
In a separate tank, transfer 49 g of steareth-6, 62 g of PEG100 stearate and heat to 60° C. Maintain the temperature till both emulsifiers become liquid. Then add 31 g of trideceth-3 and 350 g of trideceth-10 (80% of active matter). This nonionic emulsifiers mixture has an HLB value=11.25.

For Comparative Emulsion B:
In a separate tank, transfer 49 g of steareth-6, 30 g of PEG100 stearate and heat to 60° C. Maintain the temperature till both emulsifiers become liquid. Then add 300 g of trideceth-3, 100 g of trideceth-10 (80% of active matter). This nonionic emulsifiers mixture has an HLB value=8.44.

For Comparative Emulsion C:
In a separate tank, transfer 49 g of steareth-6, 350 g of PEG100 stearate and heat to 60° C. Maintain the temperature till both emulsifiers become liquid. Then add 31 g of trideceth-3, 50 g of trideceth-10 (80% of active matter). This nonionic emulsifiers mixture has an HLB value=16.474.

Step 3: Same for the 3 Emulsions
Then add 80 g water and 6.2 g glacial acetic acid in the tank and start mixing. Continue mixing till whole mass become a creamy paste. Whole paste is transfer to emulsion tank. Homogenize for 30 minutes at room temperature. Add 79.6 g demineralized water and homogenize for 60 minutes. Add 72.7 g demineralized water and homogenize for 50 minutes. Add 197.4 g demineralized water and homogenize for 5 minutes. Add 294.3 g demineralized water and homogenize for 5 minutes. Add 180 g demineralized water and homogenize for 5 minutes. Add 180 g demineralized water and homogenize for 5 minutes. Add 197.4 g demineralized water and homogenize for 5 minutes. Add 197.4 g demineralized water and homogenize for 3 minutes. Add 228.5 g demineralized water and homogenize for 3 minutes. Lastly add 40.5 g 2-phenoxyethanol as a biocide and homogenize for 3 minutes.

Results:

| | | |
|---|---|---|
| Emulsion A (HLB = 11.25) | The emulsion is stable | Particle size: 170 nm |
| Emulsion B (HLB = 8.44) | The emulsion is unstable | Particle size: 1135 nm |
| Emulsion C (HLB = 16.474) | The emulsion is unstable | Particle size: 754 nm |

The emulsion according to the invention, in which the HLB of the nonionic emulsifiers mixture is in the claimed range, is stable and has a very low particle size. This is not the case with the comparative emulsions, in which the HLB of the emulsifiers mixture is outside the claimed range.

EXAMPLE 4

Different oil-in-water emulsions have been prepared according to example 1 (HLB=11.25). All the emulsions are stable.

| | trimethylsilyl terminated dimethylsiloxane viscosity (mPa · s) at 25° C. | Aminosilicone viscosity (mPa · s) at 25° C. | Aminosilicone amine value (mg of KOH/g sample) | Particle size |
|---|---|---|---|---|
| Emulsion A (invention) | 61000 | 5600 | 7.5 | 186 nm |
| Emulsion B (comparative) | 61000 | 5000 | 1.1 | 630 nm |

-continued

|  | trimethylsilyl terminated dimethyl-siloxane viscosity (mPa · s) at 25° C. | Aminosilicone viscosity (mPa · s) at 25° C. | Aminosilicone amine value (mg of KOH/g sample) | Particle size |
|---|---|---|---|---|
| Emulsion C (comparative) | 61000 | 5700 | 20.87 | 180 nm |
| Emulsion D (comparative) | 38000 | 5600 | 7.5 | 169 nm |
| Emulsion E (comparative) | 150 000 | 5600 | 7.5 | 350 nm |

The following hair compositions were prepared (AM=active matter):

| Ingredient | % by weight |
|---|---|
| Sodium laureth sulfate (1 OE) | 13.86% AM |
| Cocoylamidopropyl betaine | 1.48% AM |
| Guar hydroxylpropyltrimonium chloride | 0.25% |
| Carbomer | 0.36% |
| Oil-in-water emulsion | 3.6% * |
| Glycerol | 0.5% |
| PEG-45M (Polyox WSR N 60 K from Dow Chemical) | 0.015% AM |
| Glycol distearate | 0.16% |
| Hexylene glycol | 0.12% |
| NaCl | 1% |
| Fragrance, preservatives | qs |
| Water | qsp 100% |

* corresponds to the quantity of emulsion as such.

Friction Test (Combing Force)

The hair swatches to be tested (1 g and 400 mm length of medium-bleached European hair SA20) are previously immersed in boiling petroleum-ether, at a range temperature of 60-80°, for 1 hour. Then they are rinsed and dried in open air.

Then, they are washed with an aqueous solution of 1% by weight of sodium lauryl ether sulfate (100 ml of solution per 2.5-3.0 gram of hair), rinsed and dried in open air.

Then, the hair swatches are washed with the composition to be tested: a quantity of 0,1 gram of the composition is applied per gram of hair; then the hair are rinsed and the friction is measured on wet hair.

The friction and combing force is evaluated by using a TA.XT plus Texture Analyzer from Stable Micro Systems Machine.

The metallic comb is attached horizontally and tightened with the screws. The hair tress is fixed within the clip of upper zig. The comb height is calibrated. The speed of the comb is 5 mm/s and the test is run for 10 times.

For fiction measurement, the hair swatch is measured by using a friction probe attachment which is 60 g of weight, the contact area with hair being approximately 1 cm², and is placed on the hair swatch and moved at a speed of 5 mm/s to measure the friction value.

The whole length of hair swatch is measured for the friction value and the friction value is obtained in grams.

The value obtained in grams could be multiplied by 400 mm length to obtain the result in g·mm.

3 swatches are measured, per composition.

The results are mentioned in the table below:

|  | Wet Friction (g · mm) | Std deviation |
|---|---|---|
| Composition containing emulsion A | 4300 | 48 |
| Composition containing emulsion B | 6560 | 151 |
| Composition containing emulsion C | 14000 | 390 |
| Composition containing emulsion D | 8495 | 138 |
| Composition containing emulsion E | 7800 | 115 |

Conclusion: the invention shows significantly better performance on wet combing properties on hair, thus improving cosmeticity of hair fibres.

The invention claimed is:

1. A hair composition comprising:
   (i) one or more surfactants, wherein the surfactants are selected from the group consisting of anionic and amphoteric surfactants, and mixtures thereof; and
   (ii) an oil-in-water emulsion having $D_{50}$ particle size of less than 350 nm, expressed in volume, and comprising:
      a silicone mixture comprising (i) one or more trialkylsilyl terminated dialkylpolysiloxanes having a viscosity of from 51,000 to 70,000 mPa·s at 25° C. and (ii) one or more amino-silicones having a viscosity of from 1,000 to 15,000 mPa·s at 25° C. and an amine value of from 3.5 to 8 mg of KOH per gram of amino-silicone;
      a mixture of emulsifiers comprising one or more nonionic emulsifiers, wherein the mixture of emulsifiers has an HLB value of about 11; and
      water,
   wherein the oil-in-water emulsion is present in the hair composition in a quantity ranging of from 0.1% to 15% by weight with respect to the total weight of the hair composition.

2. Composition according to claim 1, wherein the surfactant comprises one or more anionic surfactants, alone or as a mixture, selected from the group consisting of:
   $C_6$-$C_{24}$ alkyl sulfates;
   $C_6$-$C_{24}$ alkyl ether sulfates;
   $C_6$-$C_{24}$ alkylsulfosuccinates;
   $C_6$-$C_{24}$ alkyl ether sulfosuccinates;
   ($C_6$-$C_{24}$)acylisethionates;
   $C_6$-$C_{24}$ acylsarcosinates;
   ($C_6$-$C_{24}$)alkyl ether carboxylates;
   polyoxyalkylenated ($C_6$-$C_{24}$)alkyl(amido) ether carboxylic acids and salts thereof;
   $C_6$-$C_{24}$ acylglutamates; and
   $C_6$-$C_{24}$ acylglycinates.

3. Composition according to claim 1, wherein the surfactant comprises one or more amphoteric surfactants selected from the group consisting of:

($C_8$-$C_{20}$)alkylbetaines, sulfobetaines, ($C_8$-$C_{20}$ alkyl)amido($C_2$-$C_8$ alkyl)betaines and ($C_8$-$C_{20}$ alkyl)amido($C_2$-$C_8$ alkyl)sulfobetaines;

quaternized secondary or tertiary aliphatic amine derivatives of formula (III) or (IV):

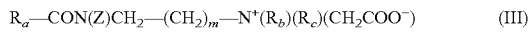

in which:

$R_a$ represents a $C_{10}$-$C_{30}$ alkyl or alkenyl group derived from an acid $R_a$—COOH, a heptyl group, a nonyl group or an undecyl group, $R_b$ represents a β-hydroxyethyl group, $R_c$ represents a carboxymethyl group;

m is equal to 0,1 or 2,

Z represents a hydrogen atom or a hydroxyethyl or carboxymethyl group;

in which:

B represents —$CH_2CH_2OX'$, with X' representing —$CH_2$—COOH, $CH_2$—COOZ', —$CH_2CH_2$—COOH, —$CH_2CH_2$—COOZ', or a hydrogen atom, B' represents —$(CH_2)_z$—Y', with z=1 or 2, and Y' representing —COOH, —COOZ', —$CH_2$—CHOH—$SO_3H$ or —CH2-CHOH—$SO_3Z'$, m' is equal to 0,1 or 2, Z represents a hydrogen atom or a hydroxyethyl or carboxymethyl group, Z' represents an ion resulting from an alkali or alkaline-earth metal an ammonium ion; or an ion resulting from an organic amine, $R_{a'}$ represents a $C_{10}$-$C_{30}$ alkyl or alkenyl group of an acid $R_aCOOH$, an alkyl group;

compounds of formula (V): $R_{a''}$—NH—CH(Y'')—($CH_2$)n-C(O)—NH—($CH_2$)n'—N($R_d$)($R_e$)

in which:

$R_{a''}$ represents a $C_{10}$-$C_{30}$ alkyl or alkenyl group of an acid $R_{a''}$—C(O)OH;

Y'' represents the group —C(O)OH, —C(O)OZ'', —$CH_2$—CH(OH)—$SO_3H$ or the group —$CH_2$—CH(OH)—$SO_3$—Z'', with Z'' representing a cationic counterion resulting from an alkali metal or alkaline-earth metal, an ammonium ion or an ion resulting from an organic amine;

$R_d$ and $R_e$ represent, independently of each other, a $C_1$-$C_4$ alkyl or hydroxyalkyl radical; and n and n' denote, independently of each other, an integer ranging from 1 to 3.

4. Composition according to claim 1, wherein the composition comprises the surfactant(s) in a total quantity ranging of from 4% to 50% by weight, with respect to the total weight of the composition.

5. Composition according to claim 1, wherein the one or more trialkylsilyl terminated dialkylpolysiloxanes are of formula (I): $R'_3SiO(R'_2SiO)_pSiR'_3$ wherein:

R', same or different, is a monovalent hydrocarbon radical having from 1 to 18 carbon atoms, and p is an integer of from 500 to 2000.

6. Composition according to claim 1, wherein the one or more amino-silicones are of formula (II):

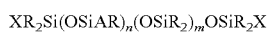

wherein:

R, same or different, is a monovalent hydrocarbon radical having from 1 to 18 carbon atoms;

X, same or different, is R or a hydroxyl (OH) or a $C_1$-$C_6$-alkoxy group;

A is an amino radical of the formula —$R^1$—[$NR^2$—$R^3$—]$_x NR^2_2$, or the protonated amino forms of said amino radical, wherein $R^1$ is a $C_1$-$C_6$-alkylene radical, $R^2$, same or different, is a hydrogen atom or a $C_1$-$C_4$-alkyl radical, $R^3$ is a $C_1$-$C_6$-alkylene radical, and x is 0 or 1;

m+n is an integer from 50 to about 1000.

7. Composition according to claim 1, wherein the one or more amino-silicones have a viscosity of from 1,500 to 15,000 mPa·s.

8. Composition according to claim 1, wherein the silicone mixture comprises (i) one or more trialkylsilyl terminated dialkylpolysiloxanes having a viscosity of from 51,000 to less than 70,000 mPa·s at 25° C. in a quantity of from 70 to 90% by weight, and (ii) one or more amino silicones having a viscosity of from 1,000 to 15,000 mPa·s at 25° C. and an amine value of from 3.5 to 8 mg of KOH per gram of amino silicone, in a quantity of from 10 to 30% by weight, relative to the total weight of the silicone mixture.

9. Composition according to claim 1, wherein the mixture of emulsifiers comprises one or more emulsifiers selected from the group consisting of:

(i) polyoxyalkylene alkyl ethers;

(ii) polyoxyalkylene ($C_8$-$C_{32}$)alkylphenyl ethers, (iii) polyoxyalkylene sorbitan ($C_8$-$C_{32}$) fatty acid esters; and (iv) polyoxyethylenated ($C_8$-$C_{32}$) fatty acid esters containing from 2 to 150 mol of ethylene oxide.

10. Composition according to claim 1, wherein the oil-in-water emulsion comprises:

the mixture of emulsifiers in a total amount of from 5 to 15% by weight, relative to the total weight of the emulsion; and/or nonionic emulsifiers in a total amount of from 5 to 15% by weight, relative to the total weight of the emulsion; and/or cationic emulsifiers in a total amount of from 0.5 to 1.5% by weight, relative to the total weight of the emulsion; and/or the silicone mixture in a total amount of from 40 to 60% by weight, relative to the total weight of the emulsion; and/or the trialkylsilyl terminated dialkylpolysiloxane(s) in a total amount of from 35 to 45% by weight, relative to the total weight of the emulsion; and/or the amino-silicone(s) in a total amount of from 5 to 15% by weight, relative to the total weight of the emulsion; and/or water in an amount of from 25 to 50% by weight, relative to the total weight of the emulsion.

11. Composition according to claim 1, wherein the oil-in-water emulsion has a $D_{50}$ particle size of from 100 to 300 nm, expressed in volume.

12. Composition according to claim 1, comprising the oil-in-water emulsion in a quantity ranging of from 0.5% to 5% by weight, with respect to the total weight of the composition.

13. Composition according to claim 1, further comprising one or more cationic polymers.

14. Composition according to claim 1, further comprising one or more oxyethylenated polymers.

15. Composition according to claim 1, comprising water in a quantity of from 40 to 99% by weight, relative to the total weight of the composition.

16. A process for cosmetic treatment of hair, comprising a step of applying to the hair the composition according to claim 1.

* * * * *